United States Patent [19]

Gulaian et al.

[11] Patent Number: 5,132,916
[45] Date of Patent: Jul. 21, 1992

[54] METHODOLOGY FOR PH TITRATION CURVE ESTIMATION FOR ADAPTIVE CONTROL

[75] Inventors: Martin Gulaian, Cleveland Heights, Ohio; David L. Lane, Vienna, Va.; Kenneth Loparo; Thomas J. Scheib, both of Chesterland, Ohio

[73] Assignee: ELSAG International B.V., Amsterdam, Netherlands

[21] Appl. No.: 526,416

[22] Filed: May 21, 1990

[51] Int. Cl.⁵ .............................................. G06F 15/46
[52] U.S. Cl. .................................... 364/502; 364/500; 436/52
[58] Field of Search ................. 364/148–152, 364/162, 496, 500, 502; 436/50, 52, 55

[56] References Cited

U.S. PATENT DOCUMENTS

| | | | |
|---|---|---|---|
| 3,730,685 | 5/1973 | Prohaska | 364/502 |
| 3,769,178 | 10/1973 | Rothermel, Jr. | 364/500 |
| 4,053,743 | 10/1977 | Niemi | 364/500 |
| 4,203,156 | 5/1980 | Ishikawa | 364/500 |
| 4,239,493 | 12/1980 | Niemi et al. | 364/500 |
| 4,302,299 | 11/1981 | Ishikawa | 364/500 |
| 4,907,167 | 3/1990 | Skeirik | 364/500 |
| 4,975,865 | 12/1990 | Carrette et al. | 364/500 |

Primary Examiner—Kevin J. Teska
Attorney, Agent, or Firm—Vytas R. Matas; Robert J. Edwards

[57] ABSTRACT

A method of estimating pH titration curves for use in the adaptive control of pH in a process, comprises gathering data points which each represent the ratio between a reagent added to the process and a flowrate to the process at a measured pH, storing the data points in a bin system according to pH, and using the stored data points to create a model of the titration curve for use in controlling the addition of reagent. Older points are replaced by newer points during the process to continuously update the model. The model was used to generate a gain schedule for operating a PI controller that is used in adding a reagent to the process.

11 Claims, 9 Drawing Sheets

METHODOLOGY FOR PH TITRATION CURVE ESTIMATION FOR ADAPTIVE CONTROL

FIELD AND BACKGROUND OF THE INVENTION

The present invention relates in general to pH control, and in particular to a new and useful method and apparatus of utilizing an estimation for a pH titration curve in the adaptive control of pH.

The control of pH is important to many processes including: boiler water treatment, chemical and biological reaction, municipal waste digestion, acid pickling/etching processes, cooling tower water treatment, electrohydrolysis, coagulation/precipitation processes, chemical reactor feeds and wastewater neutralization. Waste water treatment is especially difficult because composition is unknown and varies with time.

The control of pH is a very difficult problem. The titration curve is a plot showing pH that results from adding a given proportion of reagent. The source of the difficulty of pH control is the result of two major factors: The nonlinearity of the titration curve at any particular point in time and the time variation in the shape of the titration curve as the influent composition changes. The influent flow rate, concentrations of various acids, bases and buffering salts, and temperature change with time.

The nonlinearity of the titration curve is most acute for unbuffered acids or bases. For such cases, near a pH of 7 pH units, addition of a relatively small amount of acid or base results in a drastic change in pH. But if the pH is acidic or basic, then relatively large amounts of acid or base result in only small changes in pH. Thus when the pH is near 7 pH units, the process has an extremely high gain and when the process is not near a pH of 7 pH units, the process gain is quite small. Over the normal range of operation with strong acids or bases, it is not unexpected to have the process gain change by a factor of 10,000,000,000. Because proportional-integral (PI) controllers assume that the process is linear, the application of a classical PI controller for pH control is usually ineffective.

Because of the difficulty of pH control, many schemes include large blending volumes, batch processing, or continual operator involvement and are economically expensive.

Proposals have been made for a nonlinear PID pH controller which utilized a deadband about pH of 7 pH units and a different controller gain outside the deadband. While this controller represents an improvement over PID control for neutralization, it suffers from three major limitations: (1) it is designed only for neutralization, (2) at low buffering, it is difficult to fit the highly nonlinear pH function with such a simple function, and (3) most importantly, as the shape of the titration curve changes due to changes in acid and buffering salt composition, this method would require retuning although no provisions for tuning on-line are given.

U.S. Pat. No. 3,899,294 discloses a method for titration curve identification by simply titrating a slip stream of the main effluent stream. Then the titration curve is used to select the reagent flow rate to attain the desired pH. This procedure is relatively expensive since an automated titration system must be used to obtain the titration curve. In addition, the titration time for such an automated system may be significant in comparison to the fluid residence time in the process; therefore, when composition changes of the process stream occur, the analytical dead-time will reduce the effectiveness of the controller.

In some ways, pH control is a very simple process with a single input, a single output and easily modeled first order linear dynamics. A reagent stream is added to the incoming process stream, the two streams are mixed, and the pH is measured. The proper pH is achieved by adding the proper proportion of reagent.

What makes things so difficult is the process gain. The gain is extremely nonlinear and may change drastically if the process composition changes slightly. The gain may be so high that the output pH is hopelessly sensitive to tiny errors in the control effort. A general purpose pH controller must handle all three problems: nonlinear gain, time-varying gain, and extremely high gain.

SUMMARY OF THE INVENTION

The present invention comprises an adaptive pH controller and method of estimating a titration curve for use by such a controller, which collects a plurality of data points each comprising the ratio of reagent flowrate to influent flowrate and the observed pH at that flow rate. The points are stored in a bin system based on pH rather than time to produce a model of the titration curve. Analytical and heuristic methods are used to create the best possible model for the titration curve which is thereafter used in the adaptive control.

The present invention has been found to accurately and quickly effect pH control in a manner which closely follows the titration curve even when it has high gain characteristics and further when the titration curve changes with time as is often the case.

DESCRIPTION OF THE PREFERRED EMBODIMENT

The adaptive pH controller of the invention is an innovative attempt to solve the difficult pH control problem. Previous control schemes typically diverted the process stream into a large tank with a conservatively tuned PI controller. Difficult processes may involve a series of two or even three progressively larger tanks with independent control systems.

Figure 1:
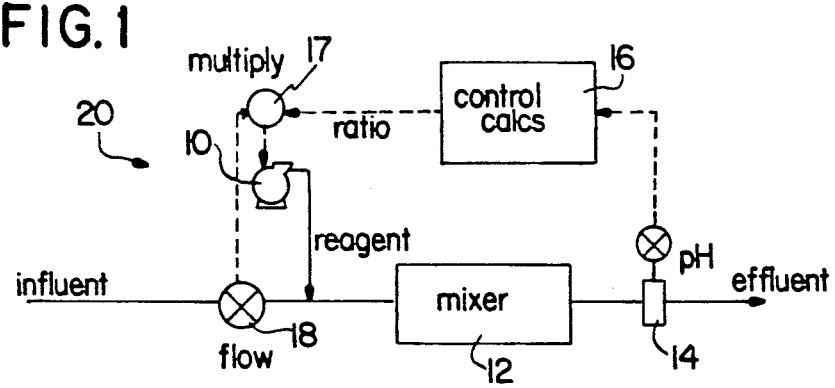
FIG. 1 is a schematic block diagram of the adaptive pH controller of the present invention.
Figure 4:
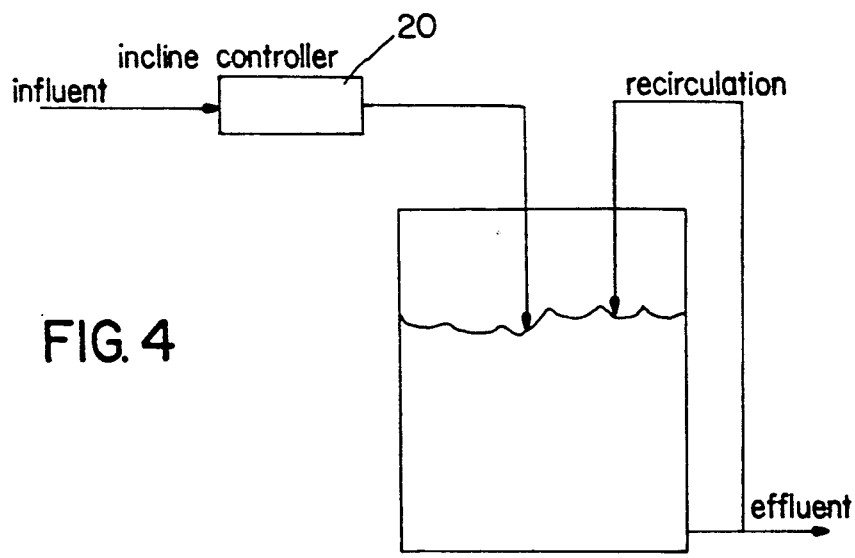
FIG. 4 is a block diagram showing the use of the controller of the invention with a downstream tank.
Figure 5:
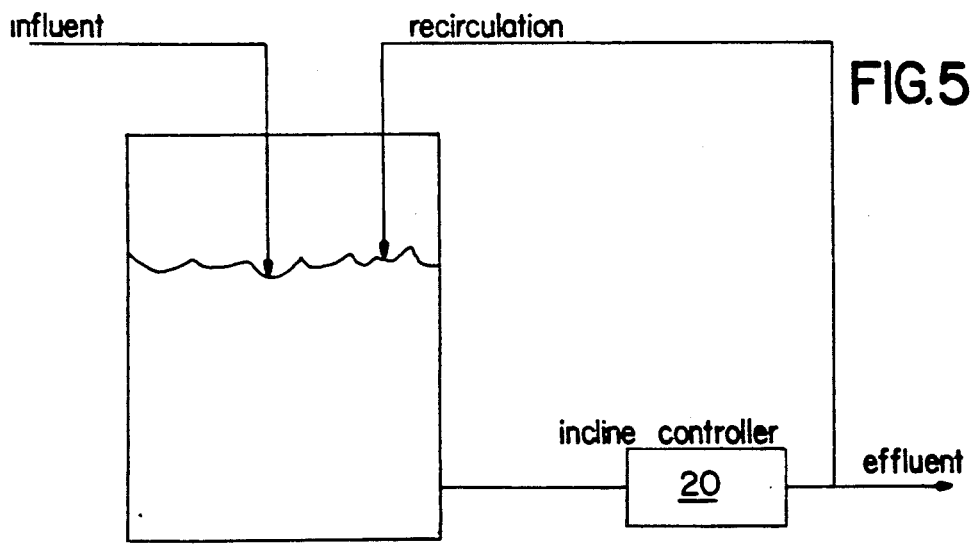
FIG. 5 is a view similar to FIG. 4 using an upstream tank.

As shown in FIG. 1 the adaptive controller 20 of the invention replaces these tanks with a small, fast inline system comprising a pump 10 to inject reagent, a small mixing element 12, and a pH probe 14 at the output of element 12. The cost savings by eliminating multiple tanks and control systems is potentially very large, and is the impetus behind developing the inline controller. Some problems may still demand a tank, but it would be much smaller than standard controllers call for. FIG. 1 shows the basic configurations. A PI controller 16 is still used to complete the loop. To compensate for load changes, a ratio controller 17 is used, with flow rate fed forward at flow meter 18. To compensate for the nonlinear system gain, a sophisticated gain schedule based on a model of the process is used. And to adapt to process changes, the process model is in turn identified online from process data by a powerful new estimation technique. Implementation of the controller includes the gain scheduled PI controller, the estimator, and a full set of heuristics to gather new data points, throw away old data points, and reconcile inconsistent data points. FIG. 4 and 5 show the placement of the inline controller 20 with tanks, FIG. 4 having a downstream tank and FIG. 5 an upstream tank.

The controller has completed a series of tests in a pH pilot plant with good test results.

Figure 3:
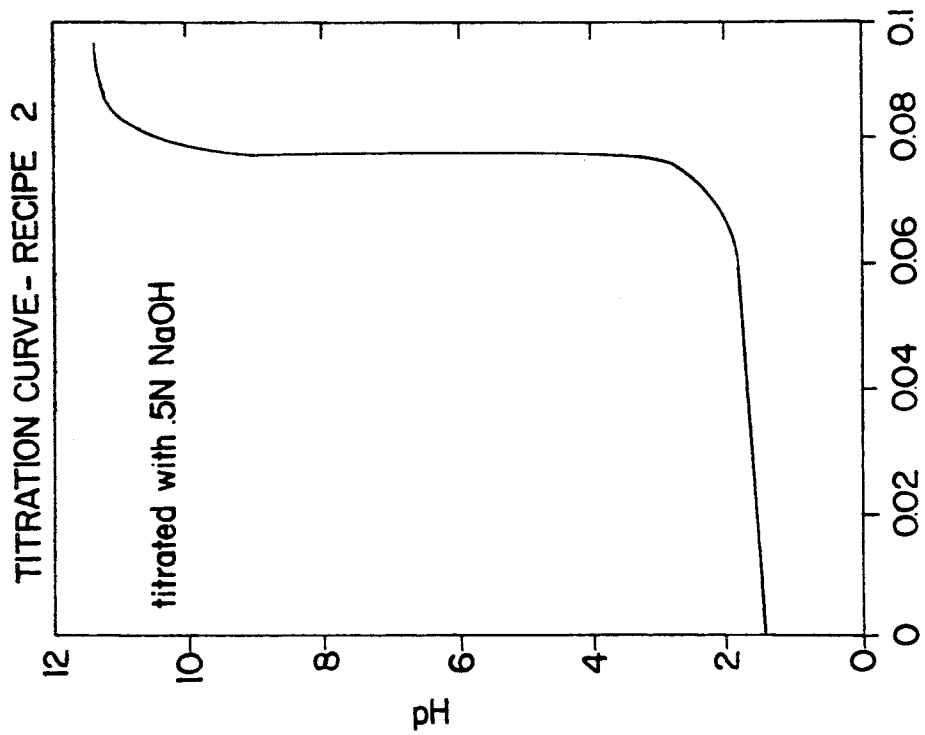
FIG. 3 is a view similar to FIG. 2 of a second recipe used in accordance with the present invention.
Figure 2:
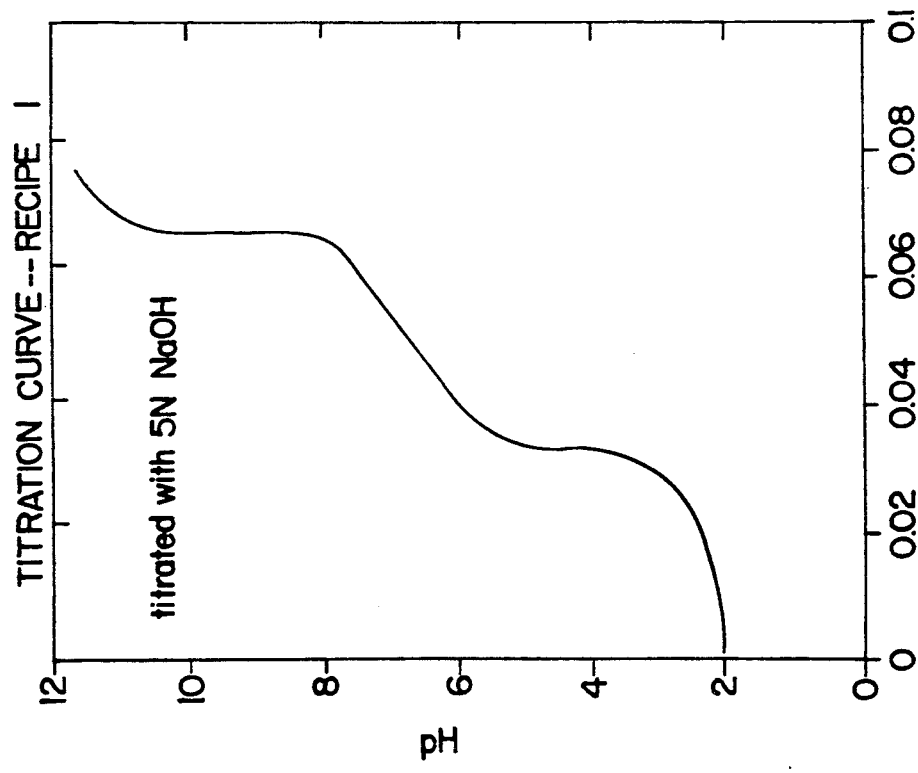
FIG. 2 is a graph showing the titration curve of a first recipe used in accordance with the present invention.

A process gain for pH is described by the titration curve; a plot showing the pH that results from adding a given proportion of reagent. FIGS. 2 and 3 show the titration curves for two chemical "recipes" used to test the pH controller of the present invention. They show a wide range of behavior: recipe 1, for example (FIG. 2), shows a low gain around the pH=7 neutral point, but a much higher gain to either side of neutral; recipe 2 (FIG. 3) shows a gain at pH =7 that is so high that the graph looks vertical. The proper controller tuning depends on the titration curve, and depends on where the setpoint falls on the curve. Given the process titration curve, a gain schedule can be derived that gives good control results with a PI controller, and the gain scheduled PI controller is now an industry standard. But the gain schedule is only as good as the titration curve it is based on, and for many applications, especially waste water neutralization, the process curve may change greatly.

The adaptive controller gathers process data to estimate a new process model for the controller gain schedule. The structure looks like this:

DATA GATHERING→MODEL ESTIMATION→GAIN SCHEDULE→PI CONTROL

The gain scheduling and PI control portions are separate from the adaptive portion. They control based on the process titration curve. For applications where the process composition is fairly constant, in chemical production for example, the titration curve may be determined offline, and only the gain schedule and PI control portions implemented online. For applications such as waste water neutralization, the process will change from hour to hour and day to day, and the data gathering and model estimation sections are needed to provide the gain scheduler with an up-to-date process model.

Converting a titration curve into a gain schedule is straightforward. Two points are found on the curve: the current operating point, and the setpoint. The points are connected to find the slope, and that is the process gain. Invert the process gain and the desired controller gain results. The mistake to avoid is taking the slope of the curve at the current operating point, which is an attempt to linearize the process. Unless the operating point is very close to the setpoint, the linearization gives a very poor match.

Figure 7:
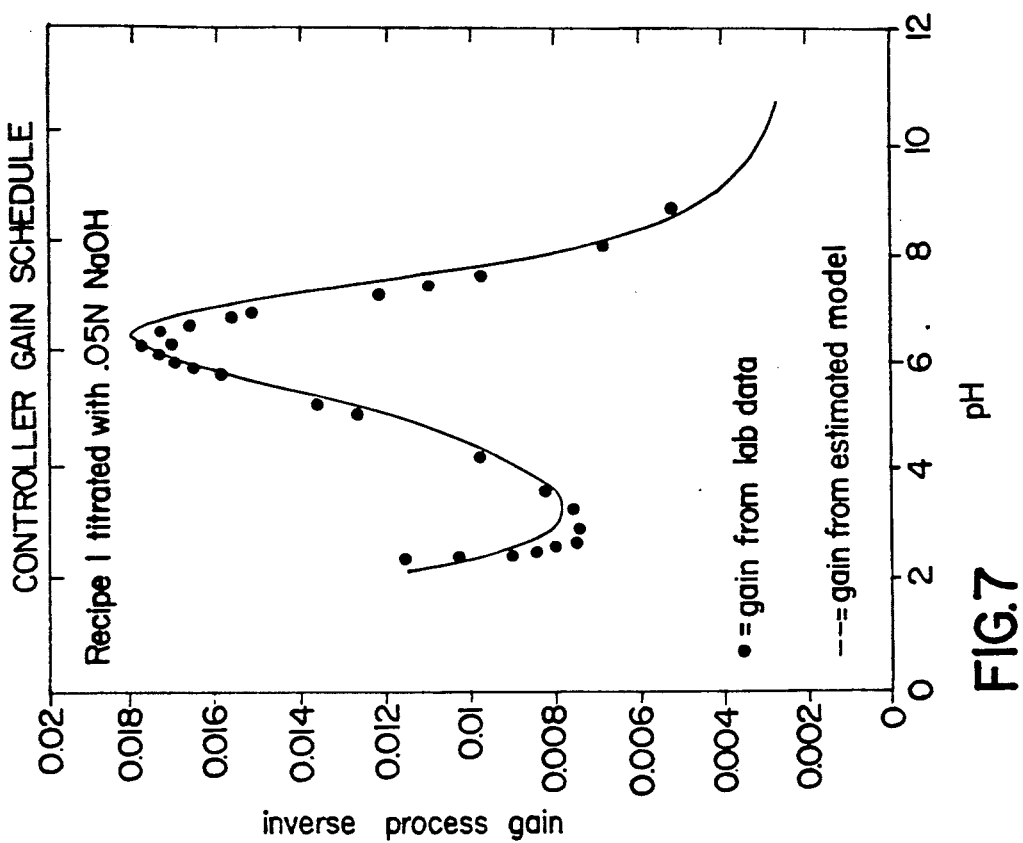
FIG. 7 is a graph showing the control gain scheme resulting from the first recipe of the present invention.
Figure 6:
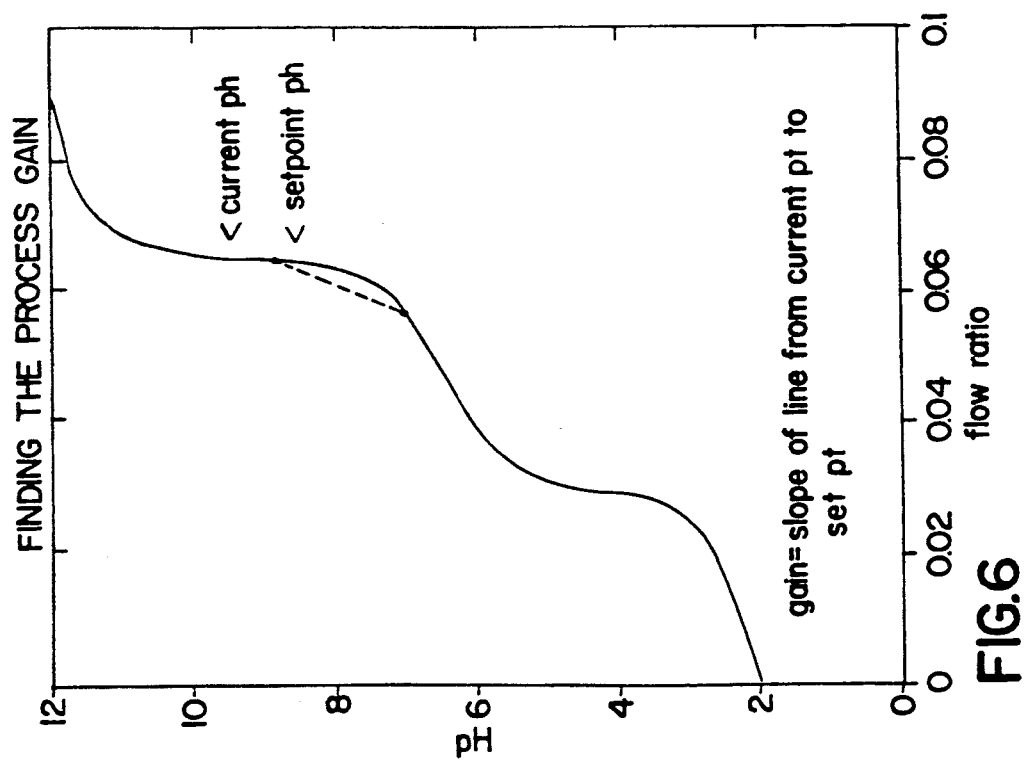
FIG. 6 is a graph illustrating the technique for obtaining a gain for use in the adaptive controller.

The gain scheduler does not store the actual titration curve. It stores a parameterized model instead, and calculates the gain directly from the parameters. FIGS. 6 and 7 show how gain is derived from the curve, and show gain schedules from the model and actual titration curve for recipe 1.

Two things determine the shape of a titration curve: the composition of the process, an the definition of pH itself. pH measures acidity, and acidity can be defined as the concentration of hydrogen ions, $[H+]$, in the solution. But pH is measured on a logarithmic scale:

$$pH = -\log_{10}([H^+]),$$

which gives pH an inherently exponential, rather than linear, character.

Furthermore, the concentration of $H+$ is a nonlinear function of reagent added, representing a complex equilibrium among all the chemical components of the process stream. Acids, bases, and salts can provide or remove $H+$ ions from the solution, fighting the effect of adding reagent and causing buffering that reduces the process gain at different pH values. Water itself disassociates into its component $H+$ and $OH^-$ ions. The relationships involved are approximately exponential, but typically include empirical correction factors which must be determined experimentally. Calculating a titration curve from chemical composition is an extremely difficult task. Attempting to back-calculate chemical composition from a titration curve is not possible. The inventive pH controller uses a simplified chemical model, but even so, identifying a process model from titration curve data is impossible. The model is simply too nonlinear and has too many parameters.

The estimation scheme of the invention tries something different. It decomposes the observed titration curve into a combination of simpler titration curves. A library of titration curves intended to span all possible process characteristics is stored. A chemical model enables one to describe each library curve with a set of stored parameters. The curves can be combined linearly to produce a composite curve. The estimator finds the linear combination of library titration curves that best fits the observed process data.

The individual library titration curves are each perfectly reasonable titration curves based on a simplified chemical model, and the model guarantees that any combination of them will be a reasonable titration curve as well. If the library curves are well chosen, a combination can be found that fits the observed data well, and can safely be extrapolated between observed data points. The same chemical model can be used to invert any combination of parameters directly into a gain schedule.

The best-fit parameters are found using a linear least squares method called singular valve decomposition (svd). Svd is a very stable solution method that enables one to fit many parameters to a few data points, and to eliminate parameters that contribute little to the fit.

Figure 8:
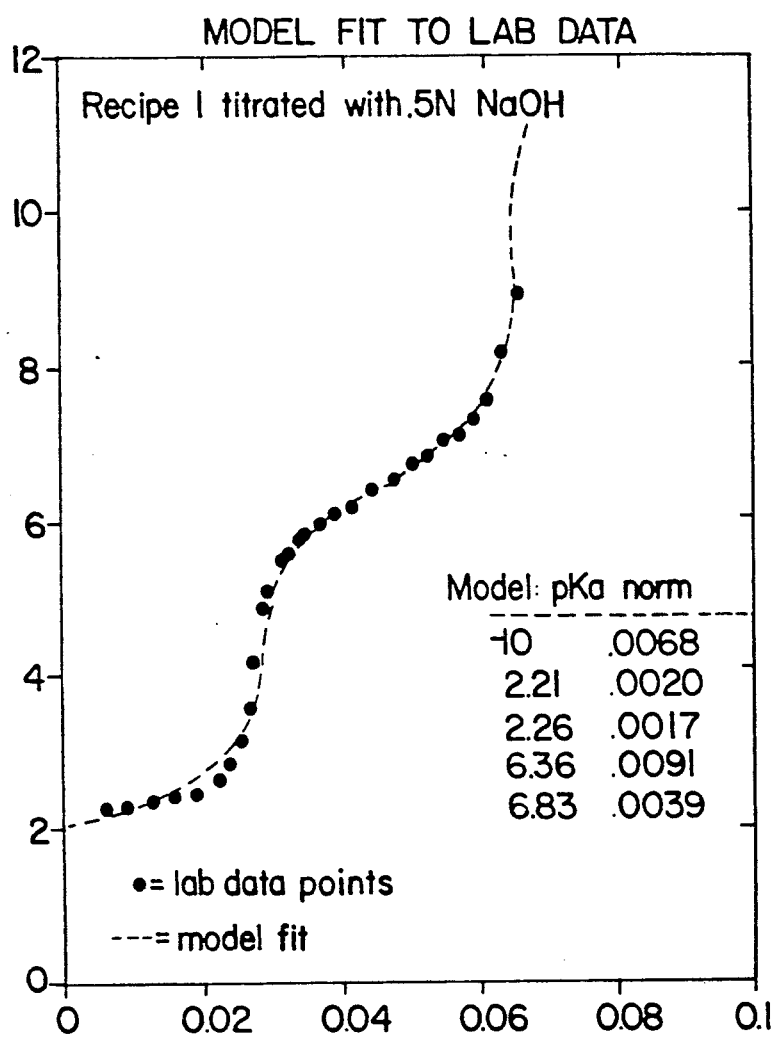
FIG. 8 is a graph showing the relationship between the actual titration curve and model titration curve obtained using the present invention.

This estimation scheme has proven to be powerful, flexible, robust, and trouble-free in extensive testinq, and is the heart of the adaptive control scheme. FIG. 8 shows the actual lab titration curve data for a recipe and the model titration curve fit to it. The 5 parameter fit is good, and the gain schedule derived from it is correspondingly good (FIG. 7).

A more detailed explanation of the math involved in estimation is disclosed later.

Given a good set of data points, the estimator can find a process model and forward it to the gain scheduler. But obtaining a good set of data points when the process is continuously and rapidly changing is difficult. By the time one gathers a new data point, all previous points may be outdated. The adaptive control design and heuristics attempts to solve this problem by gathering data as fast as possible and checking to ensure that the past data is consistent with current data.

To allow rapid data gathering, an inline configuration is used. There are no long time constants or delays due to tanks. The speed of the system is what makes data gathering possible. One can afford to wait for the system to settle out before getting a data point (because the gain of the system is nonlinear and unknown, taking data before the system reaches steady state is not suggested even if the process dynamics are well known).

Each data point consists of the ratio of reagent flow to influent flow, and the observed pH that results. There are two data gathering modes: a search mode, used on startup or when the controller is reset, and a continuous mode, used during normal control.

The search mode is used to gather an initial set of data points, or to fully replace an obsolete set of data points after a major disturbance. A binary search over the entire range of controller output is performed. Successive steps are made, always heading toward the setpoint, each step half the size of the previous step. The search concludes when the setpoint is closely bracketed, or the step size becomes too small. After each step in control output, the controller waits for pH to settle out, takes a new data point, and then makes the next step.

Continuous data gathering takes place while the controller is operating. A new point is gathered every time significant progress has been made in moving pH toward the set point, or whenever a timeout timer expires. The control output is frozen at the current flow ratio long enough for pH to settle out, and then the new point taken and the control released.

Data points are stored in a bin system based on pH, rather than in time sequence, to help build a model of the whole titration curve and to avoid problems due to lack of excitation. However, this can cause problems due to inconsistency between old and new points. There are a number of heuristics to deal with this problem:

1. Every time a new point is gathered, old data points are checked for physical consistency. Inconsistent points are eliminated.

2. If control is good (pH close to setpoint) the old model is assumed to be good: old data points are shifted in such a way that the same gain schedule is still used. This allows the controller to track process shifts which do not affect the gain schedule. Such shifts are common, caused for example by changes in reagent strength, or the addition of unbuffered material to the process stream. This also avoids problems caused by lack of excitation: if control is good the old model is unchanged.

3. If control is drastically sluggish and the pH far from the setpoint, the old model is assumed to be bad, resulting in too low a gain. Old data points are then shifted in such a way that the gain schedule gives a higher gain value at the current pH. This gives the controller a limited self-tuning ability which can help to compensate for poor data or poor controller tuning.

4. Although data points are not stored or weighted by time, they are stamped with the order in which they were taken. When control is far from the setpoint, indicating a disturbance and a changing titration curve, the oldest data points are eliminated as new points are gathered.

The heuristics deal well with the difficult problems posed by trying to track a quickly, continuously changing process, while still storing a wide range of data points to model the full titration curve and to avoid "collapse" of the estimation scheme during good control.

Every time the data set is changed, a new process model is estimated. The estimator receives the full set of data, plus a parameterized model of the reagent used. The estimator must also be given a "library" of building block titration curves which are used to decompose the process titration curve.

The best choice of library titration curves may depend on the application. In a chemical plant where the process stream is always one of few well-defined possibilities, the building block curves could be parameterized from actual samples of the process. But in the general case, the process might be anything at all. One possibility for an all-purpose set of curves is a curve which exhibits no buffering at all, and then a set of curves, each buffered at a slightly different pH value, across the entire range of pH (ph=0 to pH=14).

The set chosen for the included pilot plant tests was a set consisting of one unbuffered curve, and a set of curves with buffering at the pH valve of each observed data point. Each curve can be described by a single parameter. This has an intuitive appeal, and for small sets of data gives a much smaller set of parameters and a quicker solution. Solutions are typically found in under 1 second.

The estimator returns a process model consisting of a list of library curves, and a concentration value for the model chemical components of each curve. The model is reported to the gain scheduler and is used to compute the gain schedule until a new model is calculated.

Control is done with the pI controller 16 and the gain schedule derived from the process model. It is important to note that the process model can be obtained in different ways; in the adaptive configuration the model is found online by the estimator, but for nonadaptive problems, the model may be found offline from laboratory titration data and no online estimation done. The estimation technique of the invention may be used on any set of titration data; the inline control system described provides a method to gather that data on-line.

The PI controller is a ratio controller, using process flow rate at 18 as a fed forward multiplier. The controller must be tuned to the physical dynamics of the process, i.e. time constant and deadtime. These are functions of process flow rate. Some estimate of them must be provided to the controller. For the configuration tested, process dynamics were lumped into one parameter called settling time, which was fit as a straight line through values measured at high and low flow rates. Time constant and deadtime were assumed to be roughly equal for the inline process. Settling time is used to decide how long to freeze the control effort. Time constant and the deadtime are used for PI controller tuning, not estimation, and so are not critical to the estimation process.

The inline setup is essential for adaptive control, due to the need for speed. For nonadaptive control, any configuration can be used, with the PI controller tuned to the dynamics of the system. Since the inline system has a higher relative deadtime than a tank, a tank is easier to control and the gain scheduled controller of the invention applies more than equally well to a conventional tank setup.

The inline configuration can also be used with a tank as shown in FIGS. 4 and 5 to provide better performance. The tank is not used as a controlled vessel, however. It may be placed downstream of the controller to filter out the effect of short process disturbances and small oscillations in output pH. It may also be placed upstream of the pH controller, filtering out short process disturbances and providing a place for recirculation when output pH is out of spec.

A test regimen for the controller was devised to simulate a wide range of "real world" conditions, and to create situations which previous adaptive pH controller were unable to handle.

All tests involve neutralization of acidic waste streams. Neutralization of alkaline waste streams is an essentially identical problem. Control to a non-neutral pH is a (less difficult) subset of the neutralization problem. The test results should be valid for the general case.

The tests include startup on a range of different process streams, flow changes, concentration changes, and changes from one process to another. Both step changes and fast and slow ramp changes are used. For comparison, some tests were done using a gain schedule derived offline using the estimation technique of the invention.

A nominal control band of pH=6 to pH=9, based on typical EPA regulations, is shown on the test graphs. If pH stays inside this band control is considered adequate.

Six different process streams are used for testing. Experimental titration curves for two of them were shown in FIGS. 2 and 3. Their chemical recipes and characteristics are as follows:

| Recipe 1 | .010 M $H_3PO_4$ |
| | Low pH, low (process) gain at pH = 7, |
| | extreme gain changes. |
| Recipe 2 | .016 M $H_2SO_4$ + .022 M NaCl |
| | Low pH, high gain at pH = 7, |
| | long 'zero gain' section. |

Startups begin with a binary search, as the controller tries to find data points in the control band that bracket the setpoint. On a flat, buffered titration curve, this is easy to do. A wide range of control values fall in the control band. On a steep curve, control must fall into a tiny range, and the search will take longer and may quit without succeeding. Once the search is done, a model is fit, and PI control turned on.

Figure 9:
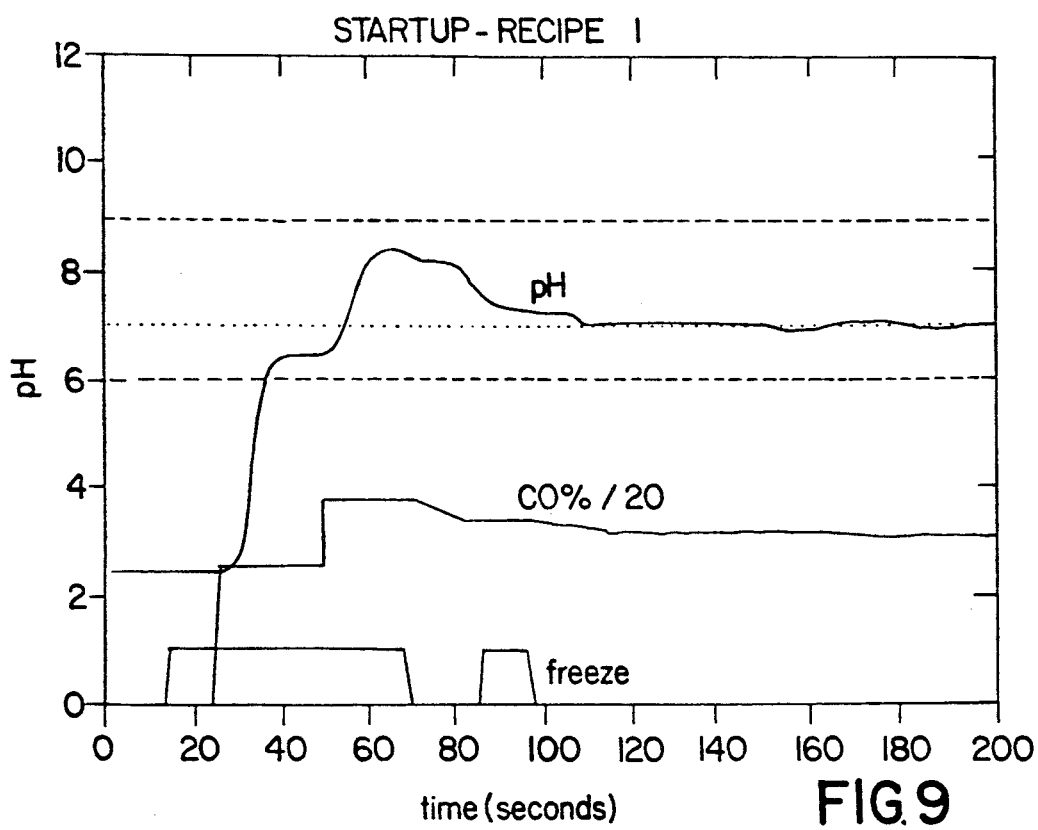
FIG. 9 shows the result of the present invention during a startup period.

Recipe 1:

Recipe 1 has a low process gain at the neutral point, allowing a higher controller gain (see titration curve, FIG. 2). FIG. 9 shows the startup. The binary search lasts only from time 10s to 70s. The PI controller was then turned on and the pH rapidly brought to the setpoint. One additional data point was gathered on the way.

The results here are very good, and are typical of controller performance where the process gain is fairly low. Low process gain makes the control band easy to find, so the binary search finishes early. Low process gain also makes the output pH insensitive to small disturbances, and allows a high feedback gain, making for better tracking of large disturbances.

Figure 10:
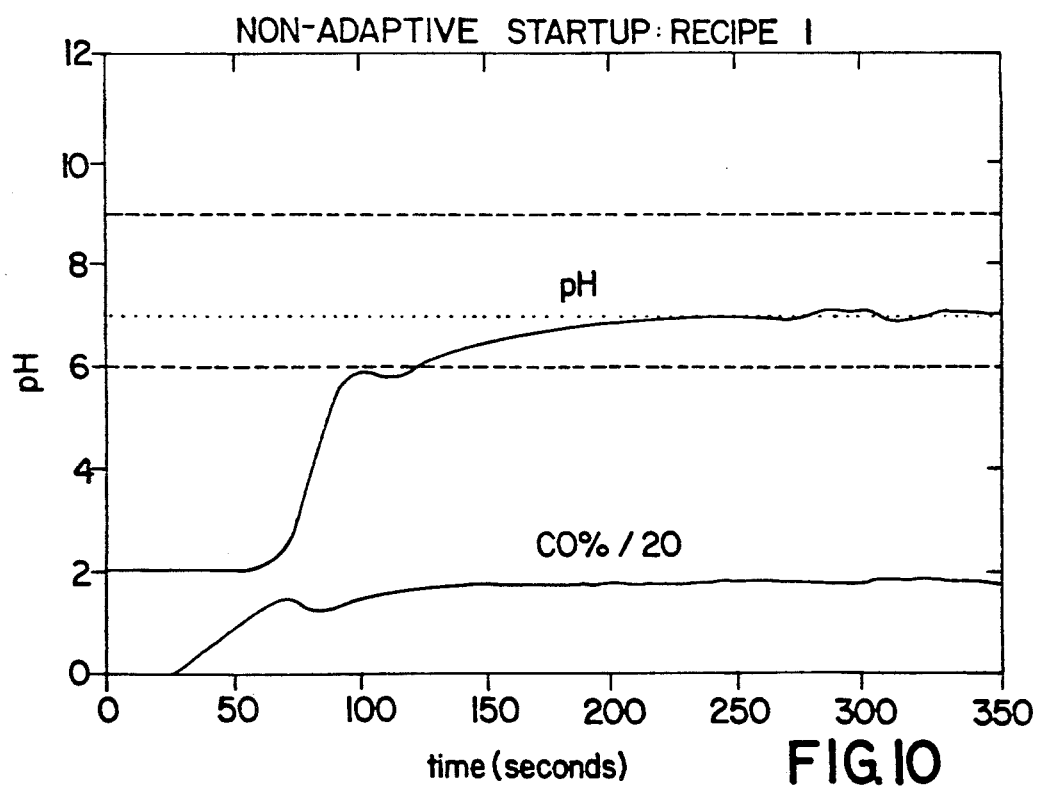
FIG. 10 is a graph similar to FIG. 9 showing the results obtained using an actual process titration curve.

For comparison, FIG. 10 shows a nonadaptive startup on the same recipe, with a gain schedule determined offline from the process titration curve. Control is good, showing that the gain scheduled PI controller can indeed compensate for the highly variable, highly nonlinear process gain.

Figure 11:
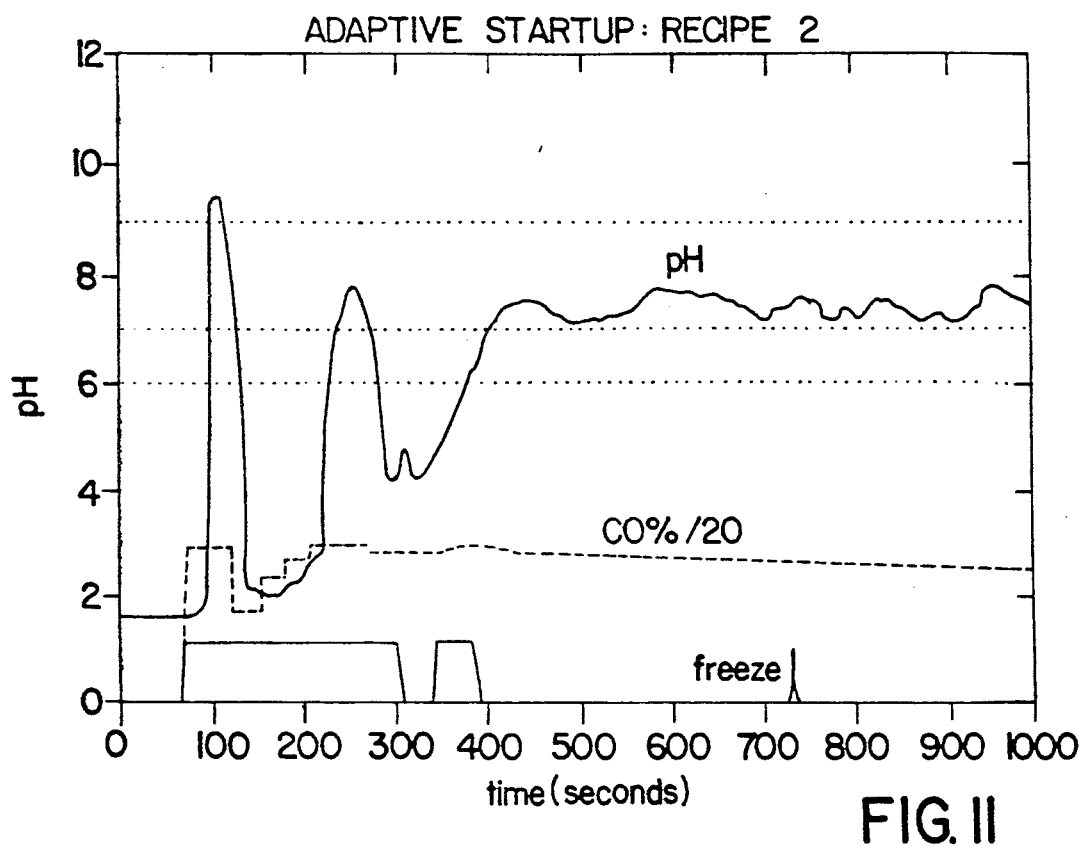
FIG. 11 is a view similar to FIG. 9 showing the results when the second recipe is utilized.

Recipe 2:

In contrast to recipe 1, recipe 2 has a very high process gain at the neutral point (titration curve, FIG. 3). FIG. 11 shows the startup. The binary search extends from time 60s to time 310s, and takes the pH through the control band several times, finally terminating at pH=4. PI control was turned on and the pH brought up. Several data points were taken along the way, and the controller gain increased in the pH 4-5 region. The pH is eventually brought close to neutral, but the system never really settles out.

Results here are typical of performance when the process gain is high (titration curve very steep). The control output must fall in a very narrow band, so the binary search process is long, and involves several excursions as the control signal overshoots the desired band in both directions. The process is very sensitive to tiny changes in process and reagent streams, amplifying noise and drift. Feedback gain is low, which makes for poor tracking of disturbances.

It should be noted that the control output is actually very close to the correct value. The titration curve shows that an error of 1 pH at the output corresponds to an error of much less than 1% at the control input. But the sensitivity of the process exaggerates the error.

Figure 12:
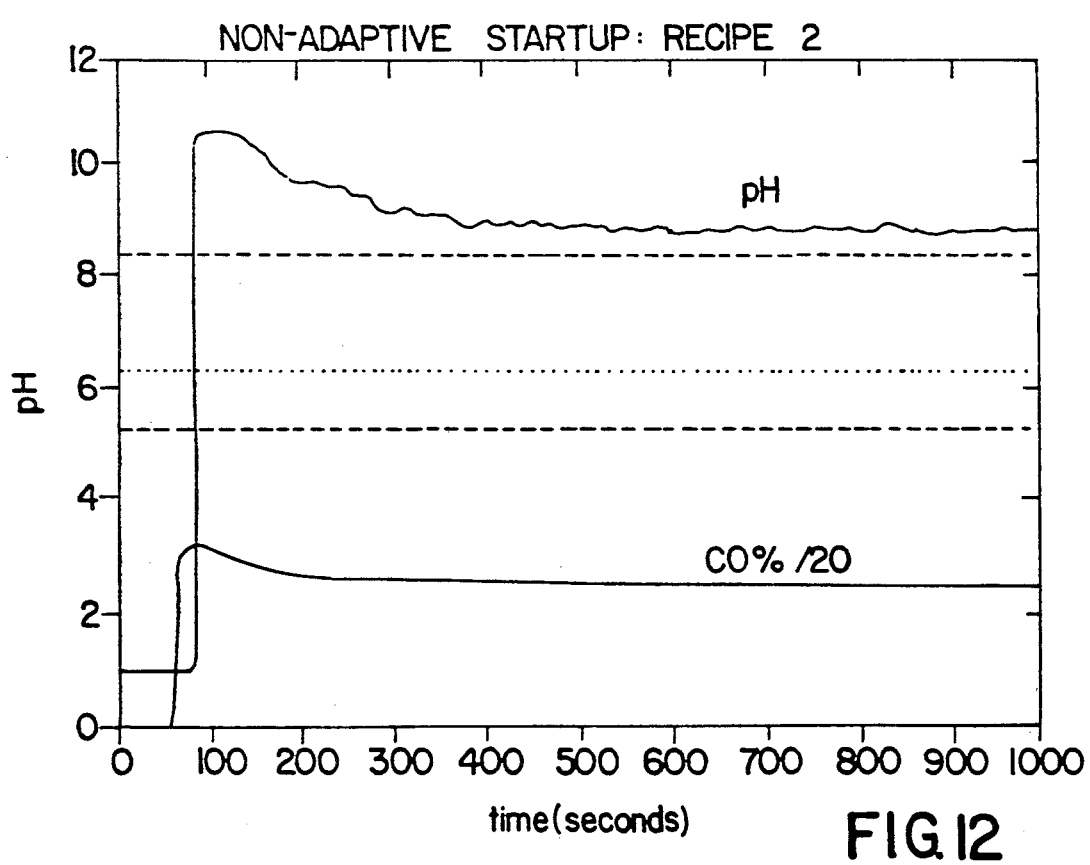
FIG. 12 is a view similar to FIG. 10 showing the results when the second recipe is utilized.

FIG. 12 shows the nonadaptive startup. The controller is tuned with a gain schedule determined offline. In this case, pH first overshoots: the titration curve steepens so fast that the lag and deadtime make the gain schedule too aggressive. But on the way back to setpoint, the opposite happens: pH gets stuck around pH=9.5 and never drops lower. The reason is that the controller gain at this pH is extremely low (see FIG. 3), and that the controller is trying to track a subtle flow rate disturbance. The waste stream is pumped from a tank, and as the tank level falls, the flow rate falls also. The disturbance is not seen in the flow rate reported to the controller, which is derived from the pump set point. The controller gain is so low that flowrate falls faster than the control output.

Concentration changes may be linked to flow rate (for example, when rain water pours into a sewer, diluting the stream and increasing the flow), or may occur independently of flow (for example, when a process that contributes a small but concentrated portion of the waste stream changes behavior). The main problem is that pH may be shifted to a part of the titration curve with a very different gain from the setpoint. A non-gain scheduled controller might get stuck, or drastically overshoot the setpoint. The gain schedule handles this problem well. Other difficulties include a process gain change proportional to the change in concentration, and a titration curve shift that makes new data points inconsistent with old ones.

Recipe 1:

Recipe 1 was tested because its titration curve shows extreme changes in gain (see FIG. 2). A change in pH puts the controller on a part of the curve that is distinctly different from where it started. The test shows a 50%, 3 minute ramp down in concentration, and then a step back up to the original value.

Figure 13:
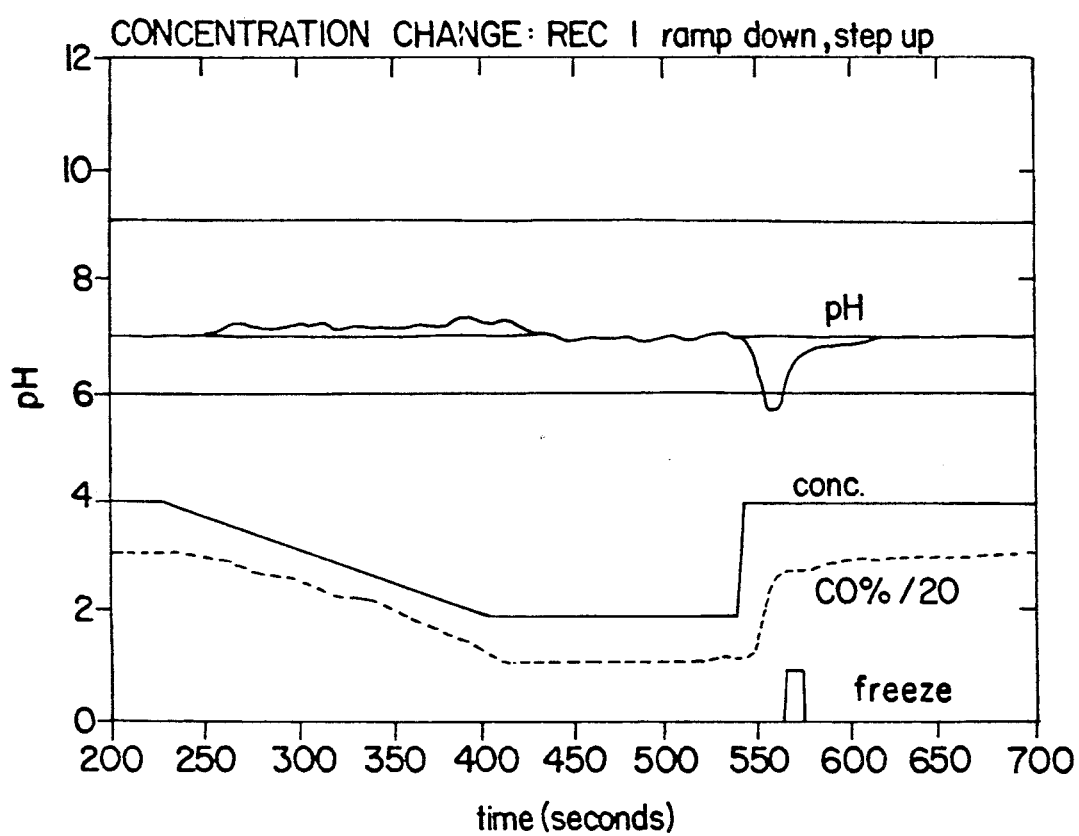
FIG. 13 shows the results of a test on the present invention involving rapid changes in concentration.

Results (FIG. 13) are very good. The process is relatively insensitive around pH=7, and the high controller gain enables the controller to track the ramp without difficulty. The step causes a sudden drop in pH, but the gain schedule handles it well, without any sign of getting stuck or overshooting.

The final set of tests involves recipe changes. Recipe changes represent a complete change in process behavior. No single gain schedule can account for the process variations seen in the test recipes. Tests included step changes, fast ramps, and slow ramps. They represent a variety of problems for the controller.

Figure 14:
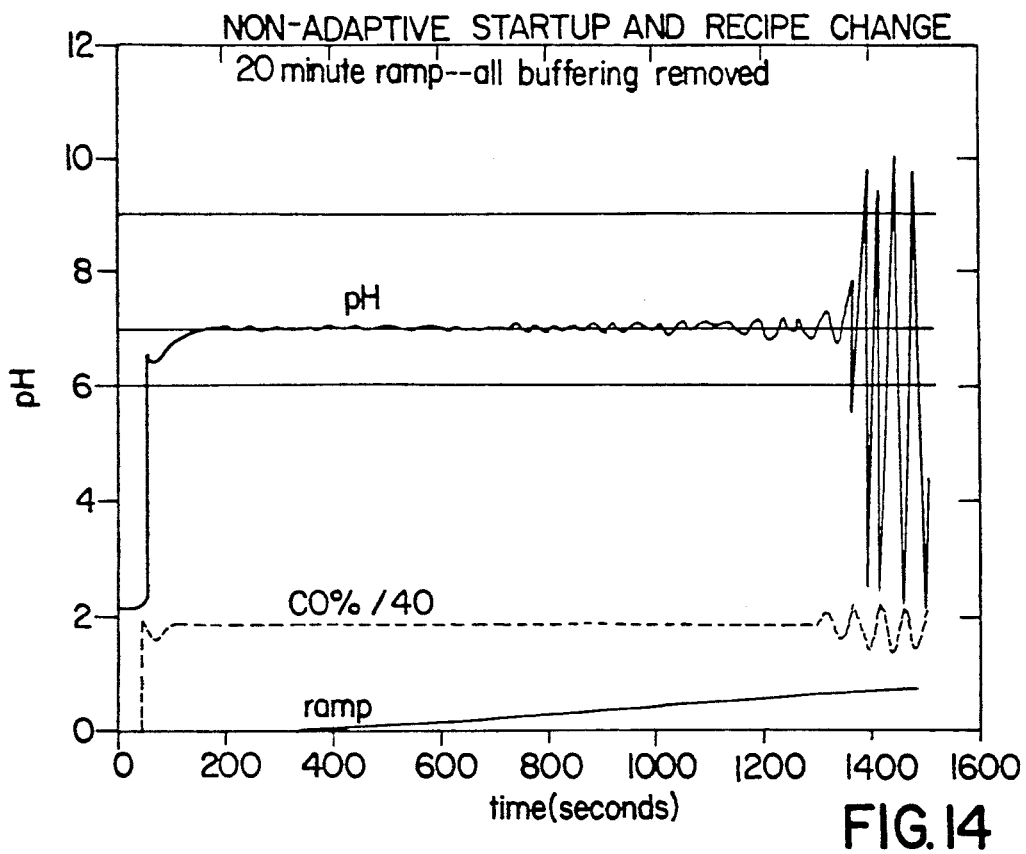
FIG. 14 shows the results of a nonadaptive controller using recipe 1 and resulting in an unstable control near the end of the cycle.
Figure 15:
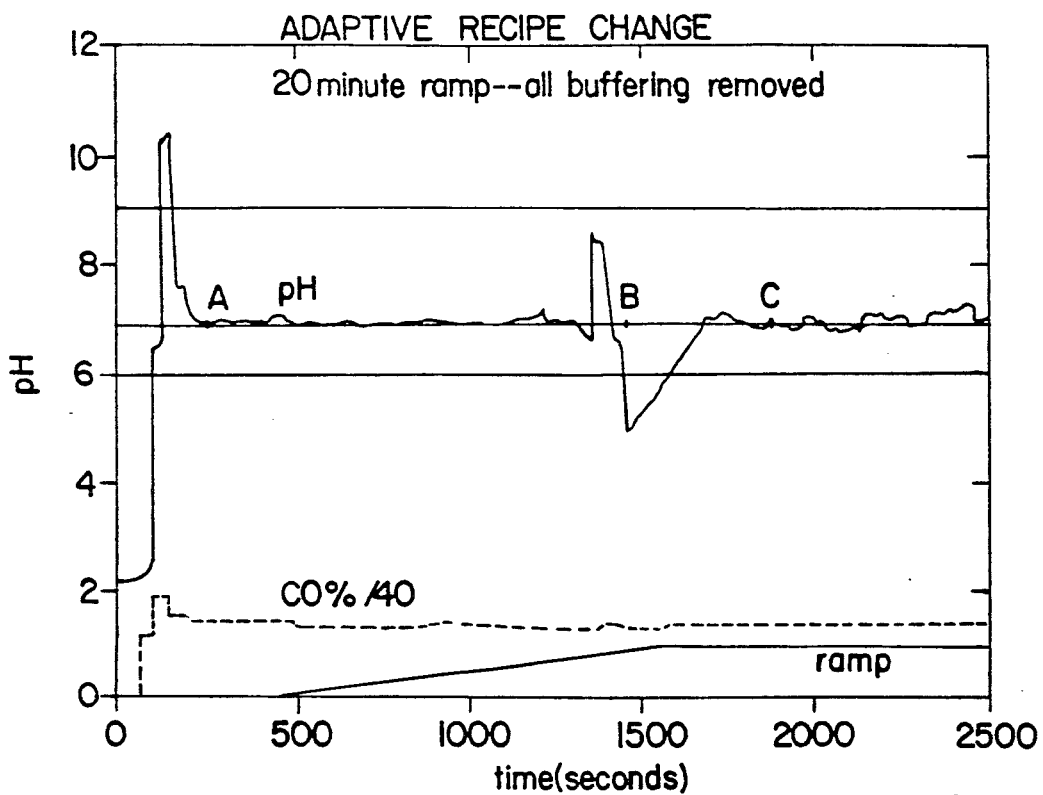
FIG. 15 is a graph showing similar results but using the present invention.
Figure 16:
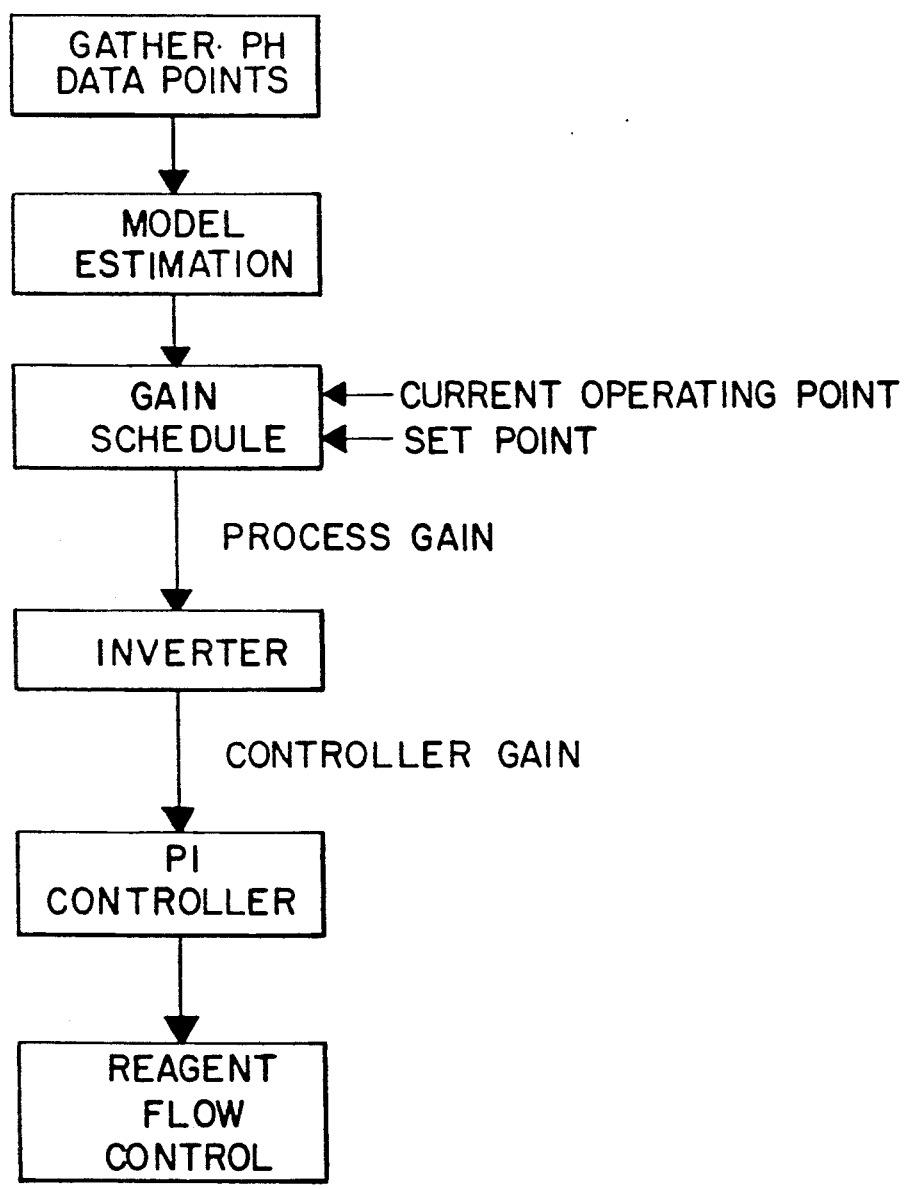
FIG. 16 is a flow char showing the control system of the present invention.

FIGS. 14 and 15 show a slow change from recipe 1 to recipe 2, with concentrations adjusted so that the control effort and outlet pH stayed the same, giving the controller no sign that the process had changed. This is a very tough test for an adaptive controller.

FIG. 14 shows the test for a non-adaptive controller, tuned for the recipe 1 titration curve. Starting at time 200s, a slow ramp between the processes is made, and the titration curve gets steeper and steeper. There is no large disturbance to force the controller into oscillation, but as the ramp progresses small oscillations start and finally go out of control.

FIG. 15 shows the same test for the adaptive controller of the invention. A binary search is performed on startup, and causes an excursion to pH 10.5, after which control is established.

The adaptive pH controller of the invention rapidly adapts to extreme process variations and load changes, requires very little tuning, and achieves pH regulation unheard of in an inline controller.

MATHEMATICS OF TITRATION CURVE ESTIMATION

Models for the chemistry of ionic solutions are well developed, but very complex, typically involving a number of experimentally derived correction factors to reconcile calculated and observed results. For control purposes, there is no need to calculate the exact behavior of a solution from its chemical composition. A simplified model can match observed process behavior adequately. The model used herein is described in Eq. (1). It ignores acidity coefficients, and assumes that all chemical reactions have reached equilibrium before pH is measured.

pH measures the activity, or effective concentration of hydrogen ions in a solution. The effective concentration may be different from the actual concentration, but in dilute solution the effect can be ignored. pH is measured as the logarithm of hydrogen ion concentration and exhibits an inherently nonlinear characteristic:

$$pH = -\log_{10}([H^+])  \quad (1)$$

where $[H^+]$ = hydrogen ion concentration, moles/liter.

Models can be written for all chemical reactions that involve hydrogen ions. These reactions include the dissociations of acids, bases, salts, and water.

Water dissociates to maintain the equilibrium product $$K_w = [H^+][OH] \quad (2)$$

$$pK_2 = -\log_{10}(K_w)$$

where, $K_w$ = ionic product for water ($10^{-14}$ at 24° C.) and $[OH^-]$ = hydroxyl ions concentration, moles/liter. Simple acids and bases dissociate in water more or less completely to form ions; the extent of dissociation is measured by a dissociation constant $K_a$ for an acid or $K_b$ for a base. For a simple acid HA and a simple base BOH they are defined:

$$K_a = [H^+][A]/[HA] \quad (3)$$

$$pk_a = -\log_{10}(Ka)$$
$$K_b = [B^+][OH]/[BOH] \quad (4)$$

$$pk_b = -\log_{10}(Kb)$$

Combining equations (3) and (4) with the definitions of pH (1) and $K_w$ (2) gives the fraction of dissociation at any given pH:

$$\text{acid: } C_a = 1/(1 + 10^{pka-ph}) \quad (5)$$

$$\text{base: } C_b = 1/(1 + 10^{pkb-pH-pK_w}) \quad (6)$$

where $C_a$ and $C_b$ range from 0 (no dissociation) to 1 (fully dissociated). The change from undissociated to fully dissociated occurs over a narrow pH range centered at $pH=pK_a$ for an acid and $pH=pK_w-pK_b$ for a base. The dissociation provides ions to neutralize added reagent, and results in buffering of the titration curve at $pH=pK_a$ or $pH=pK_w-pK_b$.

A double acid $H_2A$ (such as sulfuric acid, $H_2SO_4$) can dissociate twice, and the first and second dissociations have separate dissociation constants:

$$K_{a1} = [H+][HA]/[H_2A] \quad (7)$$

$$pK_{a1} = -\log_{10}(K_{a1})$$

$$K_{a2} = [H+][A]/[HA] \quad (8)$$

$$pK_{a2} = -\log_{10}(K_{a1})$$

The resulting formula for $C_a$ is more complex:

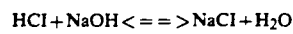
$$C_a = (1 + 5 \cdot 10^{pka1-ph})/(1 + 10^{pKa2-pH}(1+10^{pKa-pH})) \quad (9)$$

The formula for a complex base such as lime, $Ca(OH)_2$, is similar, and the formula ran be extended to triple acids and bases (such as phosphoric acid, $H_3PO_4$).

A salt results from the reaction of an acid and a base, for example:

$$HCl + NaOH <==> NaCl + H_2O$$

Salts are modeled by a mix of the component acid and base. Finally, all solutions must be electrically neutral, so a charge balance equation can be written summing the contributions of all the ionic components:

(acid ions) + (base ions) + (water ions) = 0  (10) Using the definitions developed above, this equation becomes:

$$-C_{a1}N_{a1} \ldots + C_{b1}N_{b1} + \ldots + 10^{-pH} - 10^{pH-pKw} = 0 \quad (11)$$

where
$N_{a1}$ = Normality of acid 1, etc
$N_{b1}$ = Normality of base 1, etc

Equation (11) is the basic equation used in pH estimation.

Every observed process data point represents a different chemical equilibrium involving the process components and the added reagent. The estimation problem amounts to solving a system of equations for all unknowns to identify the real process parameters. Assuming that pH is measured and pKw ($-\log_{10}([H^+][OH])$) is known, that still leaves all of the $C_a$'s and $N_a$'s, and all the $C_b$'s and $N_b$'s to be found as noted in Eq. (11) above. The $C_a$'s and $C_b$'s are nonlinear functions of the true parameters, pK$_a$ and pK$_b$. In addition, the number of components in the real process is unknown. Solving the system directly is clearly hopeless.

The idea that linearizes the problem is to assume in advance the pK$_a$'s and pK$_b$'s of the unknown process. This is the same thing as assuming that the process can be modeled as a mix of various simple acids and bases chosen in advance. Each separate pK$_a$ or pK$_b$ provides buffering to the model titration curve at the associated pH value. If the mix of pK's covers the full range of pH, it should be possible to build a titration curve with any desired degree of buffering at any desired pH, and to closely approximate the real process titration curve.

Once a set of simple acids and bases is selected, the estimation problem becomes a simple linear problem. The $C_a$'s and $C_b$'s are now known constants for each equation $$C_a = 1/(1 + 10^{pKa - pH})$$

$$C_b = 1/(1 + 10^{pH - pKb + pKw})$$

because pK$_a$ and pK$_b$ are assumed, pK$_w$ is known, and pH is measured. The amount of reagent added is known, and the corresponding pK$_a$'s and pK$_b$'s are known also, so the terms in the following equation corresponding to reagent added are constants. The estimation problem is to find the solution to a system of equations of the form:

$$C_{a1}N_{a1} + \ldots + C_{an}N_{an} + \ldots + C_{b1}N_{b1} + \ldots + C_{ba}N_{ba} = D$$

where
$C_{a1}$ through $C_{an}$ are the dissociation fractions of each preselected acid
$N_{a1}$ through $N_{an}$ are the unknown normalities of each acid
$C_{b1}$ through $C_{bn}$ are the dissociation fractions of each preselected base
$N_{b1}$ through $_{bn}$ are the unknown normalities of each base
D is a constant term lumping ions contributed from known sources (water, reagent)

Only the normality terms, corresponding to the mix of assumed acids and bases in the best fit model, need to be found, and this is a linear problem. All that is needed is enough data points to solve the system.

Computer software can convert the data points and preselected pK's to the form of the equation. The problem is then solved as a linear least squares problem, using the technique of singular value decomposition (svd). Svd enables one to find a solution even if there are fewer equations than unknowns. Although there is no unique solution to an undetermined system of equations, there is a solution of minimum magnitude, and svd can be used to find it. The result is a very stable solution to the problem that can be trusted to give reasonable answers no matter what data set is supplied. The only problem encountered is the need to force chemical normalities to be positive. An iterative procedure is used to eliminate negative normality solutions. The solution is quick and guaranteed to converge.

Furthermore, the solution can be guaranteed to behave like a real titration curve because the solution is a chemical model of the process that best fits the observed data. The combination of an estimated model based on the chemistry of the process, and a solution of minimum magnitude by singular value decomposition, makes the estimation procedure very well behaved. Most of the usual estimation problems, such as insufficient data, ridiculous parameter values due to ill conditioned data sets, or unstable extrapolation beyond the data range, have been entirely eliminated.

The desired process gain is the steady state gain, which is $$K_p = (pH_{set} - pH_{now})/(ratio_{set} - ratio_{now})$$

The set point pH is known, and the current pH is measured. What is needed is the corresponding flow ratios on the model titration curve (the measured flow ratio should not be used; mismatch between real and model titration curves can lead to absurd gain values).

The charge balance equation again is:

(acid ions) + (base ions) + (water ions) = 0 pH is known. The normality and pK values for the unmixed reagent and waste streams are both known. What is unknown is the relative proportion between the two streams that solves the equation. The dilution factors are $$D_w = w/(w + r)(\text{waste stream})$$

$$D_r = r/(w + r)(\text{waste stream})$$

where
r = reagent flow rate (gpm)
w = waste flow rate (gpm)

In the overall charge balance equation, each normality coefficient of a waste stream component must be multiplied by $D_w$, and each normality coefficient of a reagent component must be multiplied by $D_r$.

The charge balance equation becomes:

$$D_w(\text{waste ions}) + D_r(\text{reagent ions}) + (\text{water ions}) = 0$$

This is readily solved for the ratio r/w by substituting the equations for $D_w$ and $D_r$ for the dilution factors, and solving the equation with coefficients evaluated at the current pH and the setpoint pH. The gain is then determined by the equation for $K_p$.

While specific embodiments of the invention have been shown and described in detail to illustrate the application of the principles of the invention, it will be understood that the invention may be embodied otherwise without departing from such principles.

What is claimed is:

1. A method of controlling pH in a process using a PI controller wherein the gain of the controller is determined from a titration curve for the process which has a reagent added to an influent flowing at a flowrate, the method comprising:

providing a plurality of pH values, each corresponding to a ratio of reagent flowrate to flowrate of influent;

collecting a plurality of pH data points each representing a ratio between reagent flowrate and influent flowrate at the provided pH values;

storing the plurality of pH data points in a bin system based on pH;

producing a model titration curve from the pH stored data points; and using the model to establish a gain schedule for operating the gain of the controller to control the adding of the reagent to thus control the process pH.

2. A method according to claim 1 including gathering new data points and comparing each newly gathered data point with the previously collected point for consistency and, if the new data point is inconsistent with the old data point, discarding the old data point from storage.

3. A method according to claim 1 wherein the influent flows through a mixing element, the method wherein all of the collecting of the plurality of pH values are taken from the mixing element.

4. A method as set forth in claim 1 wherein the controller of the process control is an adaptive controller utilizing a heuristicly generated model.

5. A method according to claim 1 wherein the step of providing a plurality of pH values includes storing a plurality of models each produced for a separate process to create a library of stored titration curves, and fitting one of the stored curves to collected data points, to create a composite titration curve for use in controlling the pH in the controlled process.

6. A method according to claim 5 including subjecting the gathered data points to a singular value decomposition process.

7. A method according to claim 1 including gathering new data points and comparing each new data point to a set point established by a gain schedule produced from the model, the gain schedule including parameters comprising the slope of a curve between an observed condition in the process and said set point, and if agreement is good between newly gathered data points and old data points stored in the bin system, said produced model is maintained in the bin system.

8. A method according to claim 7 including each data point with an order, indicating the time that the data point was taken to distinguish newer points from older points.

9. A method according to claim 1 wherein the model to establish the gain schedule for operating the controller to add reagent to the mixing element, the gain schedule being formulated by a slope occurring between an actual operating point and a desired set point on the model.

10. A method as set forth in claim 9 wherein the gain of the controller is controlled downstream from the mixing element.

11. A method as set forth in claim 9 wherein the gain of the controller is controlled upstream from the mixing element.

* * * * *